United States Patent [19]

Westerman et al.

[11] Patent Number: 4,894,205

[45] Date of Patent: Jan. 16, 1990

[54] MULTITUBE REACTOR

[75] Inventors: David Westerman; Franciscus J. M. Schrauwen, both of Amsterdam, Netherlands

[73] Assignee: Shell Oil Company, Houston, Tex.

[21] Appl. No.: 244,234

[22] Filed: Sep. 14, 1988

[30] Foreign Application Priority Data

Sep. 18, 1987 [GB] United Kingdom ............... 8721964

[51] Int. Cl.⁴ .............................................. B01J 8/06
[52] U.S. Cl. .................................. 422/197; 261/112.1; 422/220; 422/312
[58] Field of Search ............... 422/197, 310, 312, 220; 261/112.1; 239/193, 194, 398; 196/128; 165/115, 118

[56] References Cited

U.S. PATENT DOCUMENTS

| | | | |
|---|---|---|---|
| 3,318,588 | 5/1967 | Russell et al. | 261/112.1 |
| 3,364,982 | 1/1968 | Jaffe | 261/112.1 |
| 3,884,643 | 5/1975 | Ballestra et al. | 422/197 |
| 3,918,917 | 11/1975 | Ashina et al. | 422/197 |
| 3,969,081 | 7/1976 | Jackson | 261/112.1 |
| 4,199,537 | 4/1980 | Zardi et al. | 261/112.1 |
| 4,614,229 | 9/1986 | Oldweiler | 165/115 |
| 4,683,121 | 7/1987 | Goudriaan et al. | 422/197 |
| 4,751,057 | 6/1988 | Westerman | 422/197 |

Primary Examiner—Joye L. Woodard
Attorney, Agent, or Firm—Ronald R. Reper

[57] ABSTRACT

Multitube reactor for carrying out a process for catalytic conversion, comprising a normally substantially vertically extending vessel, a plurality of open-ended reactor tubes (2) arranged in the vessel parallel to its central longitudinal axis of which the upper ends are fixed to an upper tube plate (5) and in fluid communication with a fluid inlet chamber (8) above the upper tube plate (5) and of which the lower ends are fixed to a lower tube plate and in fluid communication with an effluent collecting chamber below the lower tube plate, an inlet (13) for supplying liquid to the fluid inlet chamber (8), inlet for supplying gas to the fluid inlet chamber (8), and an effluent outlet arranged in the effluent collecting chamber, wherein the upper end part of each reactor tube is provided with a cap (25) having a gas inlet opening (27), which defines a liquid inlet (28) and an outlet (30) in fluid communication with the upper end part of the reactor tube (2), and a liquid riser (33) extending between a level in the layer (40) of liquid which is during normal operation present in the fluid inlet chamber (8) and the liquid inlet (28) of the inlet chamber (26).

6 Claims, 3 Drawing Sheets

MULTITUBE REACTOR

BACKGROUND OF THE INVENTION

The present invention relates to a multitube reactor for carrying out a process for catalytic conversion. Examples of such a conversion are the catalytic conversion of synthesis gas, comprised of carbon monoxide and hydrogen, into middle distillates and the reaction between hydrogenated acetone to form methyl isobutane and water.

Such a multitube reactor comprises a normally substantially vertically extending vessel, a plurality of open-ended reactor tubes arranged in the vessel parallel to its central longitudinal axis of which the upper ends are fixed to an upper tube plate and in fluid communication with a fluid inlet chamber above the upper tube plate and of which the lower ends are fixed to a lower tube plate and in fluid communication with an effluent collecting chamber below the lower tube plate, liquid supply means for supplying liquid to the fluid inlet chamber, gas supply means for supplying gas to the fluid inlet chamber, and an effluent outlet arranged in the effluent collecting chamber.

The upper ends of the reactor tubes are provided with tubes extending through the bottom of a horizontal tray arranged above the upper tube plate.

During normal operation the reactor tubes are filled with catalyst particles. To convert synthesis gas into middle distillates, synthesis gas s supplied through the fluid inlet chamber into the upper ends of the reactor tubes and passed through the reactor tubes. Effluents leaving the lower ends of the reactor tubes are collected in the effluent collecting chamber and removed from the effluent collecting chamber through the effluent outlet.

To distribute the heat of reaction generated during the conversion uniformly over the reactor tubes, and to improve heat transfer from the interiors of said tubes to the inner walls of the reactor tubes, liquid is introduced into the fluid collecting chamber. The liquid which is collected on the bottom of the horizontal tray flows into the upper ends of the reactor tubes. Liquid leaving the lower ends of the reactor tubes is collected in the effluent collecting chamber and removed from the effluent collecting chamber through the effluent outlet.

The heat of reaction is removed by a heat transfer fluid which is passed along the outer surfaces of the reactor tubes.

Such a multitube reactor can also be used for the catalytic conversion of a liquid in the presence of a gas.

A multitube reactor for such processes will have a diameter of about 5 m and between about 5,000 reactor tubes with a diameter of about 45 mm to 15,000 reactor tubes with a diameter of about 25 mm. The length of a reactor tube will be about 10 to 15 m.

Such a reactor will never be exactly vertical, nor will the upper tube plate be exactly flat. Consequently the distances between a horizontal plane and the upper ends of the reactor tubes will vary. As a result there are reactor tubes which during normal operation do not receive liquid. The reactions in these reactor tubes will not be adequately cooled and this will cause overheating of the reactor tubes.

It is an object of the present invention to provide a multitube reactor wherein during normal operation liquid can be substantially uniformly distributed to all reactor tubes when the reactor is slightly tilted or the upper tube plate is slightly sagged, and wherein the gas velocities in the reactor tubes are substantially insensitive to the void fractions in the reactor tubes.

SUMMARY OF THE INVENTION

To this end the multitube reactor for carrying out a process for catalytic conversion according to the invention comprises a normally substantially vertically extending vessel, a plurality of open-ended reactor tubes arranged in the vessel parallel to its central longitudinal axis of which the upper ends are fixed to an upper tube plate and in fluid communication with a fluid inlet chamber above the upper tube plate and of which the lower ends are fixed to a lower tube plate and in fluid communication with an effluent collecting chamber below the lower tube plate, liquid supply means for supplying liquid to the fluid inlet chamber, gas supply means for supplying gas to the fluid inlet chamber, and an effluent outlet arranged in the effluent collecting chamber, wherein the upper end part of each reactor tube is provided with a gas and liquid supply device, which device comprises an inlet chamber having a gas inlet opening, a liquid inlet and an outlet which is in fluid communication with the upper end part of the reactor tube, and a liquid riser extending between a level in the layer of liquid which is during normal operation present in the fluid inlet chamber and the liquid inlet of the inlet chamber.

DESCRIPTION OF PREFERRED EMBODIMENTS

It is an advantage of the multitube reactor according to the present invention that the gas and liquid supply device is insensitive to fouling. In addition, liquid can be substantially uniformly distributed to all reactor tubes even when liquid is supplied to the fluid inlet chamber at such a volumetric flow rate that the average liquid velocity in the reactor tubes is extremely low.

The invention will now be described by way of example in more detail with reference to the drawings.

Figure 1:
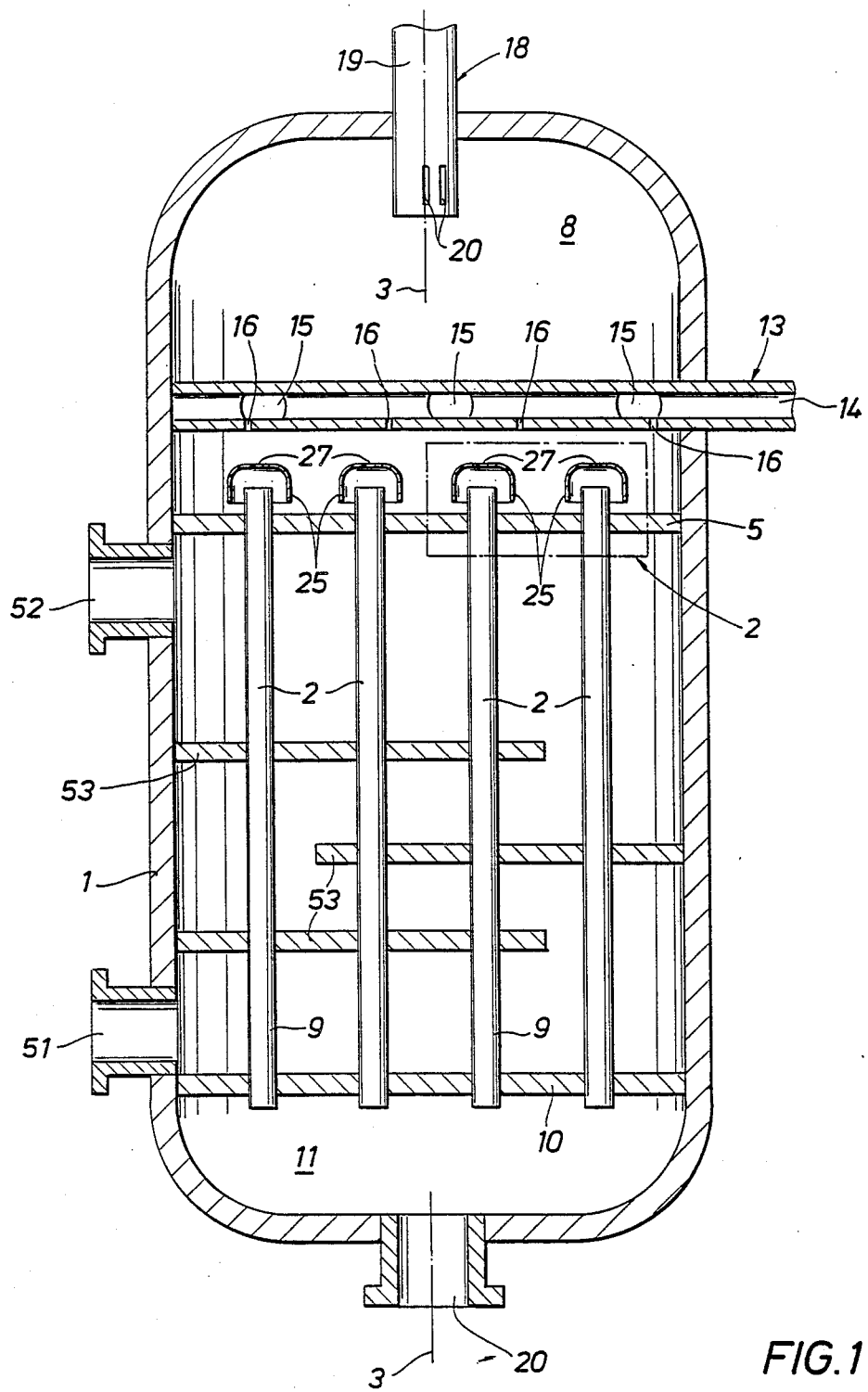
FIG. 1 shows a longitudinal section of a multitube reactor according to the invention.
Figure 2:
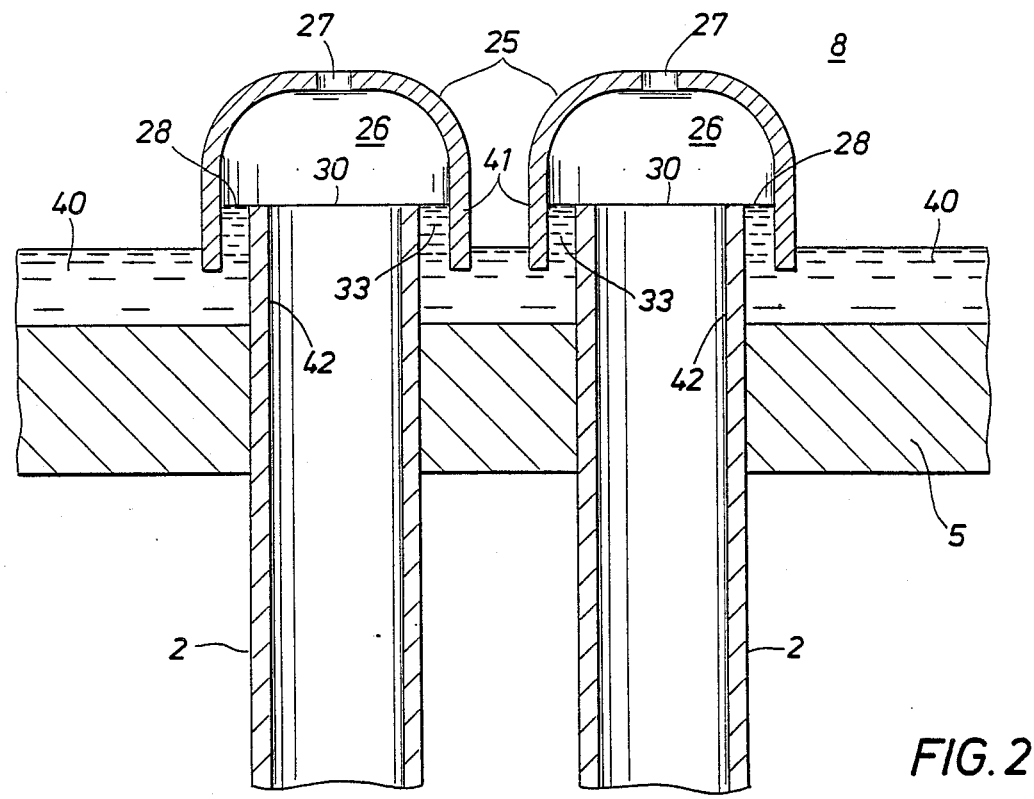
FIG. 2 shows detail II of FIG. 1 drawn to a scale larger than the scale of FIG. 1.

In FIGS. 1 and 2, the multitube reactor comprises a normally substantially vertically extending vessel 1 and a plurality of open-ended reactor tubes 2 arranged in the vessel 1 parallel to its central longitudinal axis 3.

The upper ends 4 of the reactor tubes 2 are fixed to an upper tube plate 5 which is supported by the inner wall of the vessel 1. In the upper end part of the vessel 1, above the upper tube plate 5, there is a fluid inlet chamber 8 which is in fluid communication with the upper end parts 4 of the reactor tubes. The lower end parts 9 of the reactor tubes 2 are fixed to a lower tube plate 10 supported by the inner wall of the vessel 1. In the lower end part of the vessel 1, below the lower tube plate 10, there is an effluent collecting chamber 11 which is in fluid communication with the lower ends 9 of the reactor tubes 2.

The vessel 1 is provided with liquid supply means 13 for supplying liquid to the fluid inlet chamber 8, which liquid supply means 13 comprises a main conduit 14 extending through the wall of the vessel 1 and a plurality of secondary conduits 15 extending perpendicular to the main conduit 14 and being in fluid communication with the main conduit 14. The main conduit 14 and the secondary conduits 15 are provided with outlet openings 16. The vessel 1 is further provided with gas supply means 18 for supplying gas to the fluid inlet chamber 8, in the form of a conduit 19 extending through the wall of the vessel 1 and being provided with slots 20.

In the lower part of the vessel 1 there is arranged an effluent outlet 20 communicating with the effluent collecting chamber 11.

The upper end part of each reactor tube 2 is provided with a gas and liquid supply device 25 arranged in the fluid inlet chamber 8. The gas and liquid supply device 25 comprises an inlet chamber 26 (see FIG. 2) having a gas inlet opening 27, a liquid inlet 28 and an outlet 30 which is in fluid communication with the upper end of the reactor tube 2.

The gas and liquid supply device 25 further comprises a liquid riser 33 extending between a level in the layer 40 of liquid which is during normal operation present in the fluid inlet chamber 8 and the liquid inlet 28 of the inlet chamber 26.

In the embodiments of the invention as shown in FIGS. 1 and 2 the liquid riser 33 is the annular space between a cap 41 arranged around the upper part of an extension tube 42 which is in fluid communication with the reactor tube 2, wherein the extension tube 42 is formed by the upper end part of the reactor tube 2.

During normal operation, the reactor tubes 2 which preferably are cylindrical are filled with catalyst particles (not shown), supported in the reactor tubes 2 by any conventional catalyst support means (not shown) arranged in the lower end parts of the reactor tubes 2.

To carry out a process for the catalytic conversion of gas in the presence of a liquid, or the catalytic conversion of a liquid in the presence of gas, gas and liquid are supplied to the gas supply means 18 and the liquid supply means 14, respectively. Liquid is collected on the upper tube plate 5 so that a layer 40 of liquid is formed. Gas flows through the gas inlet openings 27 of the inlet chambers 26, and consequently the pressure in the inlet chambers 26 is below the pressure in the fluid inlet chamber 8. As a result liquid is sucked from the layer 40 through the riser 33 to the liquid inlet 28. Gas and liquid pass downwardly through the reactor tubes 2 filled with catalyst particles and the conversion takes place in the reactor tubes 2. The effluents are collected in the effluent collecting chamber 11, and removed therefrom through effluent outlet 20.

If the conversion is an exothermic reaction the heat of reaction is removed by a cold fluid supplied to the heat-exchange chamber 50 through inlet 51 and removed therefrom through outlet 52. If the conversion is an endothermic reaction additional heat is supplied by a hot fluid supplied to the heat-exchange chamber 50 through inlet 51 and removed therefrom through outlet 52. In addition, the heat-exchange chamber 50 is provided with baffles 53 to guide the fluid passing therethrough.

Figure 3:
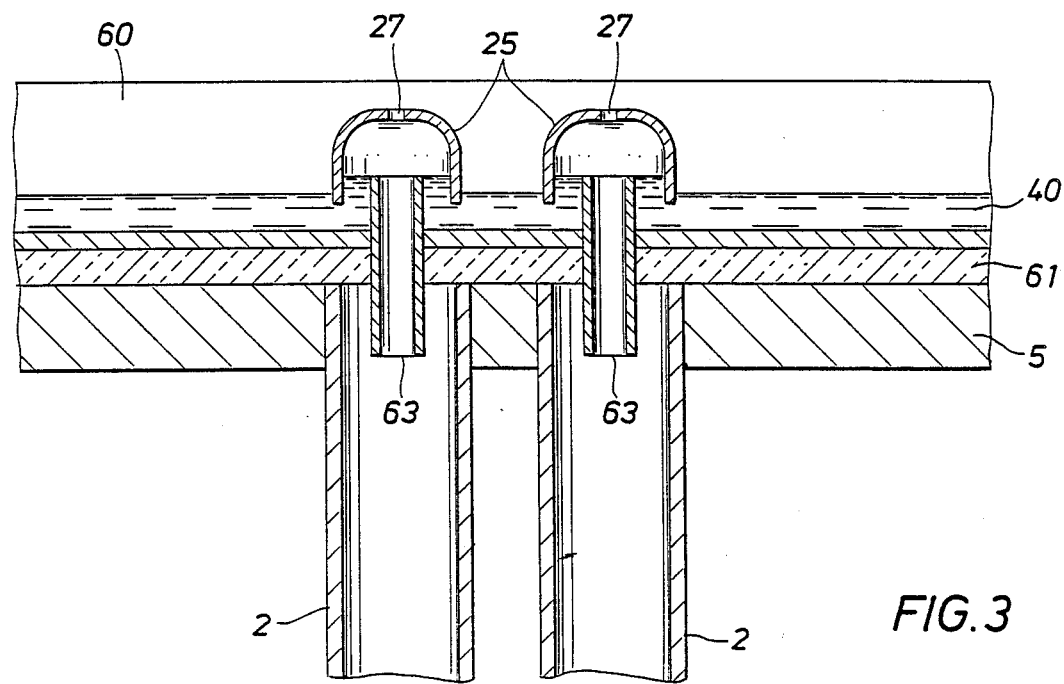
FIG. 3 shows an alternative of the gas and liquid supply device.

Reference is made to FIG. 3 showing an alternative of the apparatus as shown in FIG. 2. Parts of the device which correspond to parts shown in FIGS. 1 and 2 have the same reference numerals.

The multitube reactor is provided with a horizontal tray 60, which tray rests on an impermeable layer 61, which is supported by the upper tube plate 5. Reactor tubes 2 are provided with extension tubes 63 which pass through the impermeable layer 61 and the bottom of the horizontal tray 60.

The operation of the multitube reactor as discussed with reference to in FIG. 3 is similar to the operation of the multitube reactor as discussed with reference to in FIGS. 1 and 2.

In an alternative embodiment the impermeable layer 61 may be replaced by sealing rings (not shown) arranged in the annular zones between the inner walls of the reactor tubes 2 and the outer walls of the extension tubes 63.

Figure 4:
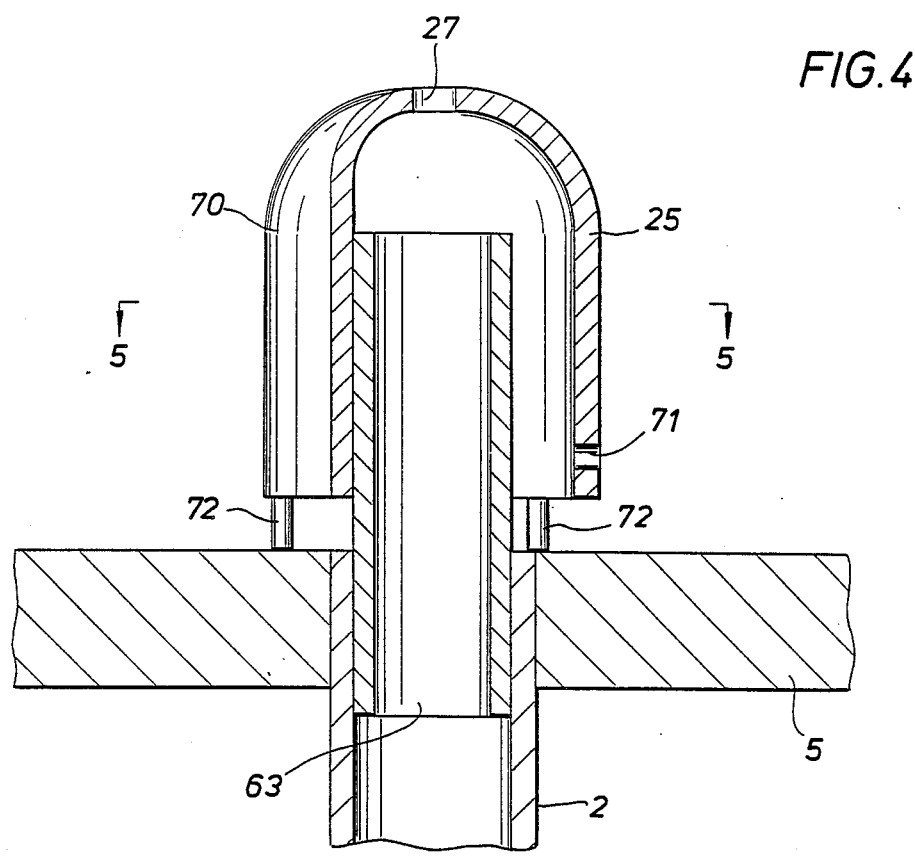
FIG. 4 shows a further alternative of the gas and liquid supply device.
Figure 5:
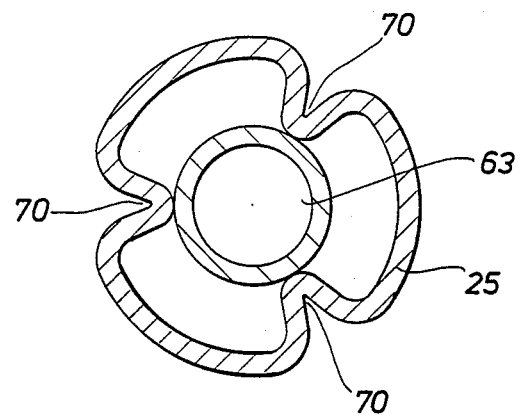
FIG. 5 shows cross-section V—V of FIG. 4.

Reference is now made to FIGS. 4 and 5 showing a further alternative of the gas and liquid supply device. Parts of the device which correspond to parts shown in FIGS. 1, 2 and 3 have the same reference numerals.

The liquid supply device 25 is provided with three longitudinal dents 70 so as to allow securing the liquid supply device on the extension tube 63.

To make the liquid supply device less sensitive to fouling, the liquid supply device 25 is provided with an opening 71 which is arranged in the layer of liquid present on the tube plate 5 during normal operation.

To facilitate positioning of the liquid supply device 25, it is provided with legs 72.

Suitably, the distance between the gas inlet opening 27 (see FIG. 2) and the outlet 30 of the inlet chamber 26 is in the range of from 0.1 to 3 times the inner diameter of the reactor tube 2.

The diameter of the gas inlet opening 27 is suitably in the range of from 2 to 30% of the inner diameter of the reactor tube 2.

EXPERIMENTS

The following experiments have been carried out using a test rig comprising a fluid distribution chamber closed at its lower end by a tube plate, and between three and five reactor tubes fixed in the tube plate and extending therethrough. The inner diameter of the reactor tubes is 24 mm, their length is 4 m, and the reactor tubes extend 0.2 m above the tube plate.

The upper end part of each reactor tube is provided with a gas and liquid supply device in the form of a cap arranged around the upper end part of the reactor tube closed at its upper end by a plate provided with a gas inlet opening, wherein the width of the annulus between the cap and the upper end part of the reactor tube is 5 mm, the distance between the gas inlet opening and the upper end of the reactor tube is 40 mm, and wherein the diameter of the inlet opening is 2.9 mm.

The lower ends of the reactor tubes debouche into a separation vessel so as to allow independent determination of the gas and liquid velocities through the reactor tubes.

Nitrogen was used to simulate the gas, and decane was used to simulate the liquid.

The expression spread of a velocity is used to refer to the ratio of the standard deviation of the velocity over the average velocity times 100%, wherein the standard deviation is the root of the average of the squares of the differences of the velocities from their average.

The first experiment was carried out to show that liquid can be substantially uniformly distributed to the reactor tubes when the reactor is tilted or the upper tube plate is sagged. To this end the test rig was provided with three reactor tubes, the upper ends of tubes 1 and 2 extended 200 mm above the tube plate and the upper end of tube 3 extended 212 mm above the tube plate. The reactor tubes were filled with spheres having a diameter of 1.5 mm, and the void fraction in the reactor tubes was 0.36 m$^3$ voids/m$^3$ bed.

Decane was supplied to the fluid inlet chamber at such a volumetric flow rate that the average liquid velocity in the reactor tubes was 0.51 mm/s. Nitrogen was supplied at such a rate that the pressure in the fluid inlet chamber was maintained at 0.53 bar (gauge).

It was found that in tube 1, the liquid velocity was 0.59 mm/s and the gas velocity 30.6 cm/s; that in tube 2, the liquid velocity was 0.62 mm/s and the gas velocity 29.6 cm/s., and that in tube 3, the extended tube, the liquid velocity was 0.32 mm/s and the gas velocity 34.2 cm/s.

The second experiment was carried out to show that liquid can be substantially uniformly distributed to the reactor tubes even when liquid is supplied to the fluid inlet chamber at such a volumetric flow rate that the average liquid velocity in the reactor tubes is extremely low. In this experiment the test rig was provided with five reactor tubes. The reactor tubes were filled with spheres having a diameter of 1.5 mm, and the void fraction in the reactor tubes was 0.36 m$^3$ voids/m$^3$ bed.

At first decane was supplied to the fluid distribution chamber at such a volumetric flow rate that the average liquid velocity in the reactor tubes was 3.3 mm/s, and nitrogen was supplied at such a rate that the pressure in the fluid inlet chamber was maintained at 0.53 bar (gauge) resulting in an average gas velocity of 17 cm/s. It was found that the spread of the liquid velocities in the tubes was 8% and that the spread of the gas velocities in the tubes was 2%.

Then decane was supplied to the fluid distribution chamber at such a volumetric flow rate that the average liquid velocity in the reactor tubes was 0.36 mm/s, and nitrogen was supplied at such a rate that the pressure in the fluid inlet chamber was maintained at 0.53 bar (gauge) resulting in an average gas velocity of 35 cm/s. It was found that the spread of the liquid velocities in the tubes was 15% and that the spread of the gas velocities in the tubes was 2%.

The third experiment was carried out to show that liquid can be substantially uniformly distributed to the reactor tubes even when liquid is supplied to the fluid inlet chamber at such a volumetric flow rate that the average liquid velocity in the reactor tubes is extremely low, and that the gas velocities in the reactor tubes are substantially insensitive to the void fractions in the reactor tubes. In this experiment the test rig was provided with five reactor tubes. The reactor tubes were filled with spheres having a diameter of 1.5 mm, and the void fractions in the reactor tubes were in the range of from 0.36 voids/m$^3$ bed.

At first decane was supplied to the fluid distribution chamber at such a volumetric flow rate that the average liquid velocity in the reactor tubes was 3.8 mm/s, and nitrogen was supplied at such a rate that the pressure in the fluid inlet chamber was maintained at 0.53 bar (gauge) resulting in an average gas velocity of 15 cm/s. It was found that the spread of the liquid velocities in the tubes was 25% and that the spread of the gas velocities in the tubes was 4%.

Then decane was supplied to the fluid distribution chamber at such a volumetric flow rate that the average liquid velocity in the reactor tubes was 0.7 mm/s, and nitrogen was supplied at such a rate that the pressure in the fluid inlet chamber was maintained at 0.53 bar (gauge) resulting in an average gas velocity 34 cm/s. It was found that the spread of the liquid velocities in the tubes was 44% and that the spread of the gas velocities in the tubes was 3%.

The presence of the gas and liquid supply means reduces the variations of the liquid velocity in the reactor tubes due to tilt of the vessel and sagging of the upper tube plate.

The fourth experiment was carried out to show the effect of the presence of the gas and liquid distributor. In this experiment the test rig was provided with four reactor tubes. The reactor tubes were filled with spheres having a diameter of 1.5 mm, and the void fractions in the reactor tubes were in the range of from 0.41 to 0.45 m$^3$ voids/m$^3$ bed.

At first decane was supplied to the fluid distribution chamber at such a volumetric flow rate that the average liquid velocity in the reactor tubes was 1.9 mm/s, and nitrogen was supplied at such a rate that the pressure in the fluid inlet chamber was maintained at 0.53 bar (gauge) resulting in an average gas velocity of 45 cm/s. It was found that the spread of the liquid velocities in the tubes was 21% and that the spread of the gas velocities in the tubes was 4%.

Then the gas and liquid distributors were removed and in four tests were reactor tube tested individually. Decane was supplied at such a rate that the liquid velocity in the reactor tubes was 2.0 mm/s, and nitrogen was supplied at such a rate that the pressure in the fluid inlet chamber was maintained at 0.53 bar (gauge) resulting in an average gas velocity of 44 cm/s. It was found that spread of the gas velocities in the tubes was 7%.

In alternative embodiment the extension tube of the gas and liquid supply means is formed by a downcomer tube extending into the upper end part of the reactor tube.

This invention has been described in detail in connection with the preferred embodiments, but these are examples only and this invention is not restricted thereto. It will be easily understood by those skilled in the art that the other variations and modifications can be easily made within the scope of this invention.

What is claimed is:

1. A multitube reactor for carrying out a process for catalytic conversion, comprising:
   a normally substantially vertically extending vessel having:
   an inner wall;
   a central longitudinal axis;
   a fluid inlet chamber disposed in the upper interior part of said vessel;
   liquid supply means for supplying liquid to said fluid inlet chamber and capable of being connected to supply of liquid;
   gas supply means for supplying gas to said fluid inlet chamber and capable of being connected to a supply of gas;
   an effluent collecting chamber disposed in the lower part of said vessel;
   outlet means in fluid communication with said effluent collecting chamber for passing reaction effluent from said vessel;
   an upper tube plate disposed in the upper part of said vessel below said fluid inlet chamber, and supported by the inner wall of said vessel;

a lower tube plate disposed in the lower part of said vessel above said effluent collection chamber and supported by the inner wall of said vessel;

a plurality of open-ended reactor tubes disposed within said vessel and parallel to its longitudinal axis for holding catalyst particles, said reactor tubes being fixed to said upper tube plate and having upper ends extending above said upper tube plate and communicating with said fluid inlet chamber, said reactor tubes having lower ends fixed to said lower tube plate, and communicating with said effluent collecting chamber; and a plurality of gas and liquid supply devices, each of said gas and liquid supply devices being disposed above the upper end of a reactor tube of said plurality of reactor tubes, each said gas and liquid supply device comprising:

a generally arcuate cap having a lower skirt extending around the uppermost portion of the upper end of said reactor tube and spaced apart from said tube thereby providing a generally annular inlet for liquid to flow from said fluid inlet chamber below said skirt to the open upper end of said reactor tube, said cap further having in its upper part an aperture for admitting gas from said fluid inlet chamber to said reactor tube, said aperture having a diameter in the range from 2 to 30% of the inner diameter of said reactor tube.

2. A multitube reactor for carrying out a process for catalytic conversion, comprising:

a normally substantially vertically extending vessel having:

an inner wall;

a central longitudinal axis;

a fluid inlet chamber disposed in the upper interior part of said vessel;

liquid supply means for supplying liquid to said fluid inlet chamber and capable of being connected to supply of liquid;

gas supply means for supplying gas to said fluid inlet chamber and capable of being connected to a supply of gas;

an effluent collecting chamber disposed in the lower part of said vessel;

outlet means in fluid communication with said effluent collecting chamber for passing reaction effluent from said vessel;

an upper tube plate disposed in the upper part of said vessel below said fluid inlet chamber, and supported by the inner wall of said vessel;

a lower tube plate disposed in the lower part of said vessel above said effluent collecting chamber and supported by the inner wall of said vessel;

a plurality of open-ended reactor tubes disposed within said vessel and parallel to its longitudinal axis for holding catalyst particles, said reactor tubes having upper ends fixed to said upper tube plate, and having lower ends fixed to said lower tube plate, and communicating with said effluent collecting chamber;

a plurality of open ended extension tubes, each of said extension tubes being disposed in a reactor tube of said plurality of reactor tubes and having a lower end disposed proximate the upper end of said reactor tube and an upper end extending above said upper tube plate;

a plurality of gas and liquid supply devices, each of said gas and liquid supply devices being disposed above the upper end of an extension tube of said plurality of extension tubes, each said gas and liquid supply device comprising:

a generally arcuate cap having a lower skirt extending around the uppermost portion of the upper end of said extension tube and spaced apart from said extension tube thereby providing a generally annular inlet for liquid to flow from said fluid inlet chamber below said skirt to the open upper end of said extension tube, said cap further having in its upper part an aperture for admitting gas from said fluid inlet chamber to said extension tube, said aperture having a diameter in the range from 2 to 30% of the inner diameter of said reactor tube.

3. Multitube reactor as in claim 2, further having a horizontal tray disposed within said vessel above said upper tube plate, and wherein said extension tubes extend through said horizontal tray.

4. Multitube reactor as in claim 2, wherein said gas and liquid supply devices have longitudinal dents securing said liquid supply devices to said extension tubes.

5. Multitube reactor as in claim 2, wherein in said gas and liquid devices the distance between said aperture and the upper end of said extension tube is in the range of from 0.1 to 3 times the inner diameter of said reactor tube.

6. A multitube reactor for carrying out a process for catalytic conversion, comprising:

a normally substantially vertically extending vessel having:

an inner wall;

a central longitudinal axis;

a fluid inlet chamber disposed in the upper interior part of said vessel;

liquid supply means for supplying liquid to said fluid inlet chamber and capable of being connected to supply of liquid;

gas supply means for supplying gas to said fluid inlet chamber and capable of being connected to a supply of gas;

an effluent collecting chamber disposed in the lower part of said vessel;

outlet means in fluid communication with said effluent collecting chamber for passing reaction effluent from said vessel;

an upper tube plate disposed in the upper part of said vessel below said fluid inlet chamber, and supported by the inner wall of said vessel;

a lower tube plate disposed in the lower part of said vessel above said effluent collecting chamber and supported by the inner wall of said vessel;

a plurality of open-ended reactor tubes disposed within said vessel and parallel to its longitudinal axis for holding catalyst particles, said reactor tubes being fixed to said upper tube plate and having upper ends extending above said upper tube plate and communicating with said fluid inlet chamber, said reactor tubes having lower ends fixed to said lower tube plate, and communicating with said effluent collecting chamber; and a plurality of gas and liquid supply devices, each of said gas and liquid supply devices being disposed above the upper end of a reactor tube of said plurality of reactor tubes, each said gas and liquid supply device comprising:

a generally arcuate cap having a lower skirt extending around the uppermost portion of the upper end of said reactor tube and spaced apart from said tube thereby providing a generally annular inlet for liquid to flow from said fluid inlet chamber below said skirt to the open upper end of said reactor tube, said cap further having in its upper part an aperture for admitting gas from said fluid inlet chamber to said reactor tube, said aperture having a diameter in the range from 2 to 30% of the inner diameter of said reactor tube, and the distance between said aperture and the upper end of said reactor tube is in the range of 0.1 to 3 times the inner diameter of said reactor tube.

* * * * *